US011559312B2

(12) United States Patent
Itoh et al.

(10) Patent No.: US 11,559,312 B2
(45) Date of Patent: Jan. 24, 2023

(54) EMBOLUS MATERIAL AND METHOD OF MANUFACTURING THE SAME

(71) Applicant: TERUMO KABUSHIKI KAISHA, Tokyo (JP)

(72) Inventors: Yuki Itoh, Hadano (JP); Eri Ikuno, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/036,081

(22) Filed: Sep. 29, 2020

(65) Prior Publication Data

US 2021/0015492 A1 Jan. 21, 2021

Related U.S. Application Data

(63) Continuation of application No. PCT/JP2019/011706, filed on Mar. 20, 2019.

(30) Foreign Application Priority Data

Mar. 29, 2018 (JP) .............................. JP2018-063998

(51) Int. Cl.
*A61B 17/12* (2006.01)
*A61B 17/00* (2006.01)
*A61L 31/14* (2006.01)

(52) U.S. Cl.
CPC .. *A61B 17/12186* (2013.01); *A61B 17/00234* (2013.01); *A61B 17/12113* (2013.01);
(Continued)

(58) Field of Classification Search
CPC ........ A61B 17/12186; A61B 17/00234; A61B 17/12113; A61B 17/1219;
(Continued)

(56) References Cited

U.S. PATENT DOCUMENTS 4,890,612 A * 1/1990 Kensey .............. A61B 17/0057
606/213
8,292,918 B2 * 10/2012 Hill .................... A61B 17/0057
606/213
(Continued)

FOREIGN PATENT DOCUMENTS

JP  2002539853 A  11/2002
JP  2004537353 A  12/2004
(Continued)

OTHER PUBLICATIONS

International Search Report (with English Translation) and Written Opinion issued in corresponding International Patent Application No. PCT/JP2019/011706, 7 pages (dated Jun. 11, 2019), considered as disclosed.

(Continued)

*Primary Examiner* — Phong Son H Dang
(74) *Attorney, Agent, or Firm* — Buchanan Ingersoll & Rooney PC

(57) ABSTRACT

An embolic material which prevents flow of a biological fluid by being placed in a body lumen via a catheter, the embolic material comprising a material that swells by contacting the biological fluid. The embolic material includes a long filler that is formed smaller than an inner diameter of the catheter. The filler prevents the flow of the biological fluid by bending when brought into contact with the biological fluid due to the difference in swelling characteristics between a first side portion and a second side portion that extend parallel to one another in a longitudinal direction.

20 Claims, 16 Drawing Sheets

(52) U.S. Cl.
CPC ........... *A61L 31/145* (2013.01); *A61L 31/146* (2013.01); *A61B 2017/00292* (2013.01); *A61B 2017/00526* (2013.01)

(58) Field of Classification Search
CPC ........ A61B 17/12118; A61B 17/12145; A61B 17/12109; A61B 17/0057; A61B 2017/1205; A61B 2017/00292; A61B 2017/00526; A61B 2017/00938; A61B 2017/00898; A61B 2017/00942; A61L 15/60; A61L 27/52; A61L 27/54; A61L 31/00; A61L 31/145; A61L 31/146; A61L 31/148; A61L 24/00; A61L 24/001; A61L 24/0031; A61L 24/0036; A61L 2430/36; A61L 2400/04
USPC ......................................................... 606/200
See application file for complete search history.

(56) References Cited

U.S. PATENT DOCUMENTS

| | | | | |
|---|---|---|---|---|
| 8,858,592 | B2* | 10/2014 | Stopek | A61B 17/0057 606/213 |
| 2003/0233150 | A1* | 12/2003 | Bourne | A61F 2/0036 623/23.72 |
| 2005/0155608 | A1* | 7/2005 | Pavcnik | A61B 17/0057 128/831 |
| 2006/0034930 | A1* | 2/2006 | Khosravi | A61L 26/0052 424/484 |
| 2006/0276831 | A1* | 12/2006 | Porter | A61B 17/1215 606/200 |
| 2007/0207186 | A1* | 9/2007 | Scanlon | B29C 55/26 623/1.42 |
| 2007/0299464 | A1 | 12/2007 | Cruise et al. | |
| 2008/0109017 | A1* | 5/2008 | Herweck | A61F 2/0063 606/151 |
| 2009/0022770 | A1* | 1/2009 | Andersson | A61L 27/20 424/423 |
| 2010/0280546 | A1* | 11/2010 | Campbell | A61B 17/0057 606/213 |
| 2011/0015613 | A1 | 1/2011 | Anzai | |
| 2012/0101519 | A1 | 4/2012 | Hill et al. | |
| 2014/0135812 | A1 | 5/2014 | Divino et al. | |
| 2015/0342581 | A1* | 12/2015 | Mylonakis | A61L 24/0031 606/214 |
| 2016/0278785 | A1 | 9/2016 | Connolly et al. | |

FOREIGN PATENT DOCUMENTS

| | | |
|---|---|---|
| JP | 2010500917 A | 1/2010 |
| JP | 2010-162063 A | 7/2010 |
| JP | 2011507637 A | 3/2011 |
| JP | 2013505791 A | 2/2013 |
| WO | 2009122971 A1 | 10/2009 |

OTHER PUBLICATIONS

Coppi, G., et al, "Transealing: A Novel and Simple Technique for Embolization of Type 2 Endoleaks Through Direct Sac Access From the Distal Stent-graft, Landing Zone," European Journal of Vascular and Endovascular Surgery, 47:4, pp. 394-401 (Apr. 2014).

The extended European Search Report dated Feb. 26, 2021, by the European Patent Office in corresponding European Patent Application No. 19775299.1-1122. (10 pages).

English Translations of the International Search Report (Form PCT/ISA/210) and the Written Opinion of the International Searching Authority (Form PCT/ISA/237) dated Jun. 11, 2019, by the Japanese Patent Office in corresponding International Application No. PCT/JP2019/011706. (5 pages).

* cited by examiner

EMBOLUS MATERIAL AND METHOD OF MANUFACTURING THE SAME

CROSS-REFERENCES TO RELATED APPLICATIONS

This application is a continuation of International Application No. PCT/JP2019/011706 filed on Mar. 20, 2019 which claims priority to Japanese Patent Application No. 2018-063998 filed on Mar. 29, 2018, the entire content of both of which is incorporated herein by reference.

FIELD OF THE INVENTION

The present invention generally relates to an embolus material that is indwelled in a biological lumen and inhibits flow of a biological fluid and a method of manufacturing the embolus material.

BACKGROUND DISCUSSION

To inhibit flow of a biological fluid (for example, blood) in a biological lumen, a known treatment has involved indwelling an embolus material in the biological lumen. Specifically, there are methods that involve injecting a liquid embolus material that is solidified when coming into contact with a biological fluid into a biological lumen, and methods that involve indwelling a bead-like or thread-like embolus material in a biological lumen via a catheter or the like.

Japanese Patent Application Publication No. 2002-539853 (JP-T-2002-539853), Japanese Patent Application Publication No. 2004-537353 (JP-T-2004-537353), Japanese Patent Application Publication No. 2011-507637 (JP-T-2011-507637), and Japanese Patent Application Publication No. 2013-505791 (JP-T-2013-505791) disclose methods of indwelling an embolus material.

A method of injecting a liquid embolus material is disclosed in "A Novel and Simple Technique for Embolization of Type 2 Endoleaks Through Direct Sac Access From the Distal Stent-graft Landing Zone", G. Coppi et-al., European Journal of Vascular and Endovascular Surgery, Volume 47 Issue 4 p. 394 to 401, April/2014.

SUMMARY

However, in the method of indwelling a liquid embolus material in a biological lumen, there is concern that an embolus material before being solidified may flow along with a flow of a biological fluid to move from a desired portion and to embolize an unintended location such that a new complication is caused. There is also concern that a bead-like or thread-like embolus material may move from a desired position due to a flow of a biological fluid in the same manner as the liquid embolus material.

Disclosed here is an embolus material can inhibit a flow of a biological fluid at a desired position without movement thereof due to the flow of the biological fluid and a method of manufacturing the embolus material.

According to one aspect, there is provided an embolus material that is indwelled in a biological lumen to inhibit a flow of a biological fluid in the biological lumen. The embolus material includes an elongated filling body that is made of a material that swells when brought into contact with the biological fluid, wherein the elongated filling body possesses opposite ends spaced apart from one another along a longitudinal extent of the elongated filling body, with the elongated filling body including a first side portion and a second side portion that both extend along the longitudinal extent of the elongated filling body and that are relatively positioned in a radial direction of the elongated filling body. The first side portion and the second side portion each have swelling characteristics, with the swelling characteristics of the first side portion of the elongated filling body being different from the swelling characteristics of the second side portion of the elongated filling body.

According to the embolus material, since the long filling body is curved due to the difference in swelling characteristics, a curved portion is caught at a biological lumen, and thus it is possible to prevent movement of the embolus material due to a flow of a biological fluid. As a result, the embolus material stays to be swollen at a desired position and can thus inhibit a flow of a biological fluid.

In the embolus material, the difference in swelling characteristics may be a difference in swelling rate. As mentioned above, in a case where there is a difference in swelling rate between the first side portion and the second side portion, a curved structure is formed due to a length difference between the first side portion and the second side portion in the process of the filling body being swollen. Consequently, it is possible to prevent movement of the embolus material due to a flow of a biological fluid.

In the embolus material, the difference in swelling characteristics may be a difference in equilibrium swelling degree. As mentioned above, in a case where there is a difference in equilibrium swelling degree between the first side portion and the second side portion, a length difference between the first side portion and the second side portion is maintained in a state in which the filling body is swollen, and thus a curved state is maintained even after the filling body is swollen. Consequently, it is possible to prevent movement of the embolus material due to a flow of a biological fluid.

In the embolus material, a surface area of the first side portion may be larger than a surface area of the second side portion. Consequently, a water infiltration rate of the first side portion is higher than a water infiltration rate of the second side portion, and thus a swelling rate of the first side portion is relatively high. As a result, a curve is formed in the swelling process of the embolus material, and thus it is possible to prevent movement of the embolus material due to a flow of a biological fluid.

In the embolus material, a porous density of the first side portion may be higher than a porous density of the second side portion. In this case, a surface area of the first side portion increases, and thus a swelling rate of the first side portion is higher than a swelling rate of the second side portion.

In this case, a pore forming agent that is leached to form a porous structure by coming into contact with the biological fluid may be contained on a first side portion side of the filling body.

In the embolus material, insoluble particles that are not dissolved in the biological fluid may be contained on a second side portion side of the filling body. The insoluble particles can reduce a swelling rate of the second side portion by hindering infiltration of water into the filling body. In other words, a swelling rate of the first side portion is higher than a swelling rate of the second side portion, and thus a curve can be formed in the embolus material.

In the embolus material, a thread-like or thread-shaped structure made of a material having an equilibrium swelling degree lower than an equilibrium swelling degree of the filling body may be included on the second side portion side of the filling body. The second side portion including the thread-like structure causes curving since a swelling ratio of the filling body is low.

In the embolus material, the second side portion may be covered with a waterproof film. Consequently, an area of the second side portion contacting water is reduced, and thus a swelling rate of the second side portion can be reduced. In other words, a swelling rate of the first side portion is higher than a swelling rate of the second side portion, and thus a curve can be formed in the embolus material.

In the embolus material, an ionic strength of the first side portion may be higher than an ionic strength of the second side portion. A water infiltration rate is high in a portion having a high ionic strength, and thus a swelling rate of the first side portion can be made higher than a swelling rate of the second side portion.

According to another aspect, there is provided a method of manufacturing an embolus material that is indwelled in a biological lumen to inhibit a flow of a biological fluid, the method including a step of preparing a raw material solution for a hydrogel containing a plurality of compositions; a step of unevenly distributing some of the compositions in a part of the raw material solution; and a step of fixing uneven distribution of some of the compositions by polymerizing the raw material solution to form a hydrogel.

In the method of manufacturing an embolus material, the raw material solution may contain water-soluble particles or water-insoluble particles as an additive, and the additive is unevenly distributed by precipitating the additive.

In the method of manufacturing an embolus material, the raw material solution may contain particles having a surface potential as an additive, and the additive is unevenly distributed by applying an electric field to the raw material solution.

In the method of manufacturing an embolus material, a porous portion may be formed in a part of the hydrogel by eluting the additive after the hydrogel is formed.

In the method of manufacturing an embolus material, the raw material solution may contain a polyelectrolyte, and the polyelectrolyte is unevenly distributed by applying an electric field to the raw material solution.

The embolus material according to the aspects can inhibit a flow of a biological fluid at a desired position without movement thereof due to the flow of the biological fluid. According to the method of manufacturing the embolus material, it is possible to obtain the embolus material that can inhibit a flow of a biological fluid at a desired position without movement thereof due to the flow of the biological fluid.

According to another aspect, a method of inhibiting flow of a biological fluid in a biological lumen comprises: inserting a distal end of a catheter into the biological lumen so that the distal end of the catheter is positioned in the biological lumen, with the distal end of the catheter positioned in the biological lumen including an interior in which is located an embolus material. The embolus material located in the interior of the distal end of the catheter is comprised of an elongated filling body that is made of a material that swells when brought into contact with the biological fluid. The elongated filling body is elongated along a longitudinal extent of the elongated filling body and possesses opposite ends spaced apart from one another along the longitudinal extent of the elongated filling body. The elongated filling body includes a first side portion and a second side portion that both extend along the longitudinal extent of the elongated filling body, with the first side portion and the second side portion each having swelling characteristics, and the swelling characteristics of the first side portion of the elongated filling body being different from the swelling characteristics of the second side portion of the elongated filling body. The method additionally includes pushing the embolus material out of the interior of the distal end of the catheter to position the embolus material in the biological lumen. The embolus material in the biological lumen contacts the biological fluid in the biological lumen to cause the elongated filling body to swell, and the swelling of the elongated filling body causes the elongated filling body to deform into a configuration different from the configuration of the elongated filling body when the embolus material is located in the interior of the distal end of the catheter by virtue of the difference in swelling characteristics of the first side portion of the elongated filling body relative to the second side portion of the elongated filling body.

DETAILED DESCRIPTION

Set forth below with reference to the accompanying drawings is a detailed description of embodiments of an embolus material and method of manufacturing an embolus material representing examples of the inventive embolus material and manufacturing method disclosed here.

First Embodiment

Figure 1A:
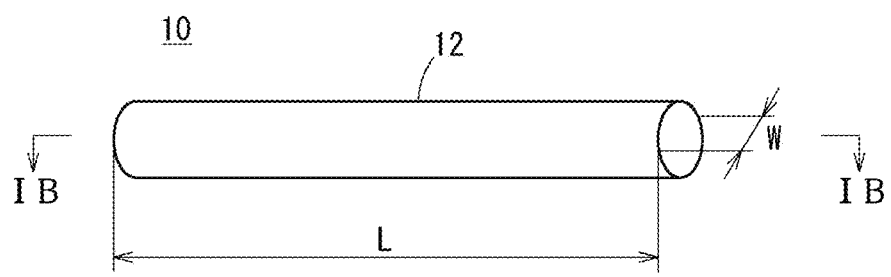
FIG. 1A is a perspective view illustrating an embolus material according to a first embodiment of the present invention.

As illustrated in FIG. 1A, an embolus material 10 according to the present embodiment disclosed as an example of the inventive embolus material includes an elongated filling body 12. The filling body 12 is inserted into or positioned in a blood vessel of a living body via a catheter 90 (refer to FIGS. 5A to 5C), and a width W of the filling body 12 is smaller than an inner diameter of the catheter 90 to be used in a state before the filling body is swollen (dried state or non-swollen state). The width W is, for example, about 0.2 mm to 2 mm. A length L of the filling body 12 is 0.5 cm to 100 cm in the dried state. The filling body 12 is formed in an elongated shape in which a ratio (L/W) of the length L to the width W is 2 or greater. A longitudinal cross-sectional shape of the filling body 12 is not limited to the illustrated rectangular shape, and may be a shape such as a circular shape, an elliptical shape, or a polygonal shape. The filling body 12 may be formed in a tubular shape of which a central portion is hollow.

The filling body 12 is made of a hydrogel that is expanded through contact with water in a biological fluid. The hydrogel is a polymer material that is swollen by absorbing water, and has polymer chains crosslinked in a three-dimensional mesh shape. In a dried state, the polymer chains are in an entangled state. When water molecules diffuse into the polymer chains, the polymer chains are loosened, and thus the mesh structure is dilated by containing the water molecules and is thus swollen.

As the hydrogel, a polyacrylic acid, a polymethacrylic acid, a polyacrylamide, a polyhydroxyethyl methacrylate and derivatives thereof, a crosslinked polymer of a polyol such as a polyvinyl alcohol, a polyvinylpyrrolidone, or a polyethylene glycol, or a polysaccharide-based hydrogel may be used.

Figure 1B:
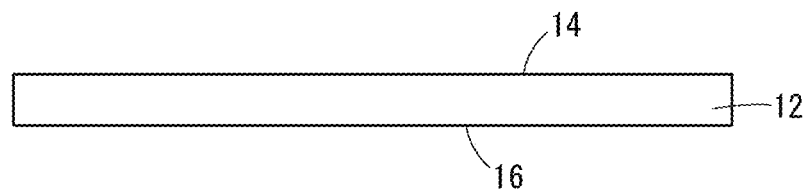
FIG. 1B is a cross-sectional view taken along the section line IB-IB in FIG. 1A.

The filling body 12 has a difference in swelling characteristics between a first side portion 14 extending in a longitudinal direction of the filling body 12 and a second side portion 16 extending parallel to the first side portion 14 in a longitudinal cross-sectional view of FIG. 1B. In the present embodiment, when focusing on a swelling rate as one of the swelling characteristics of the hydrogel, a swelling rate of the hydrogel is changed between the vicinity of the first side portion 14 and the vicinity of the second side portion 16. In other words, the swelling rate of the hydrogel at the first side portion 14 of the elongated filling body 12 differs from the swelling rate of the hydrogel at the second side portion 16 of the elongated filling body 12.

Specifically, the first side portion 14 is provided with a plurality of slits with a predetermined depth, and is formed such that a surface area of the first side portion 14 is larger than a surface area of the second side portion 16. With this configuration, an infiltration rate of water from the first side portion 14 is higher than an infiltration rate of water from the second side portion 16. A swelling rate of the hydrogel increases as the infiltration rate of water increases. Thus, in the process of the filling body 12 being swollen, the first side portion 14 becomes transitionally longer than the second side portion 16 to cause curving.

Figure 2A:
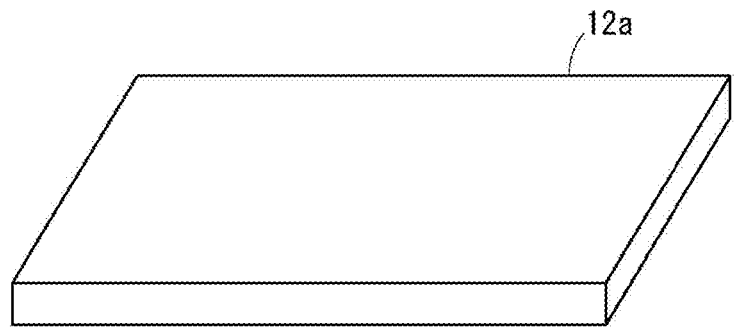
FIGS. 2A, 2B, and 2C are perspective views illustrating a method of manufacturing the embolus material in FIG. 1A in a step order.
Figure 2B:
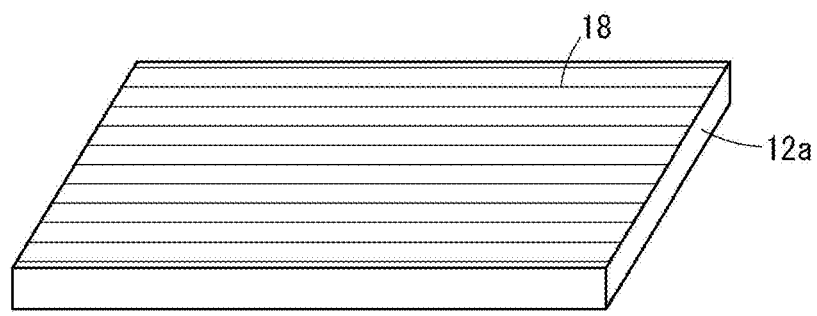
Figure 2C:
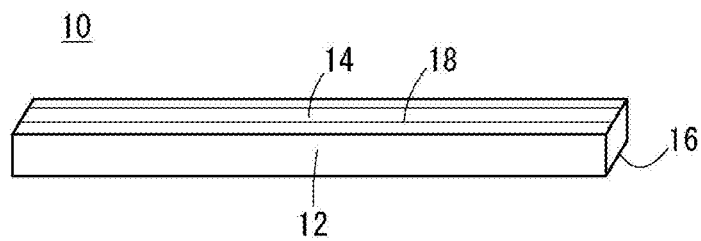

The embolus material 10 may be manufactured according to steps illustrated in FIGS. 2A to 2C. First, as illustrated in FIG. 2A, a thin plate-shaped hydrogel 12a is formed. The hydrogel 12a may be produced, for example, by crosslinking ethylenically unsaturated monomers with radiation, heat, a redox agent, a nucleophile, or the like. A raw material solution for the hydrogel may contain an ethylenically unsaturated monomer, a crosslinking agent that forms a crosslinking structure, and a suitable solvent. The raw material solution is poured into a mold.

Herein, as the ethylenically unsaturated monomer, a 2-hydroxyethyl methacrylate, a hydroxybutyl acrylate, a t-butylacrylamide, an N,N'-methylenebisacrylamide, an N-vinylpyrrolidinone, an N-isopropylacrylamide, an acrylic acid, and an ethylenically unsaturated carboxylic acid having a hydroxyl group, a sulfuric acid group, a salt thereof, an amino group, and/or an ammonium group may be used.

The crosslinking agent is a compound containing a branched molecule having at least two functional groups, and, for example, an ester, a carbonate, a thioester, a carbamate, an oxalate, a thioester, an N,N'-methylenebisacrylamide, and an ethylene glycol dimethacrylate may be used.

The ethylenically unsaturated monomer in the raw material solution is polymerized by a stimulus such as ionizing radiation, ultraviolet light, or heat, to form a hydrogel, but the raw material solution may contain a polymerization initiator that generates a free radical to initiate a reaction as necessary. As the polymerization initiator, for example, azobisisobutyronitrile (AIBN) or derivatives thereof may be used.

The raw material solution may contain a visualization agent for checking an indwelling position 94a of the embolus material 10 in a blood vessel 94 or for checking a state after the embolus material is indwelled. The visualization agent may be introduced according to a method in which solid particles containing an element such as barium sulfate, bismuth, tantalum, platinum, or gold through which radiation is hardly transmitted are dispersed in the hydrogel. The visualization agent may be introduced according to a method in which an organic compound containing an atom having a large atomic number such as chlorine, bromine, or iodine may be polymerized into a polymer.

As the solvent, for example, isopropyl alcohol, dichloromethane, acetone, water, ethanol, or a combination thereof may be used.

After the raw material solution is poured into the mold, the thin plate-shaped hydrogel 12a illustrated in FIG. 2A is formed by polymerizing the raw material solution according to a method of heating the raw material solution with a heating medium such as hot water (100° C.) for several hours, or a method of irradiating the raw material solution with ionizing radiation or ultraviolet rays.

Figure 3A:
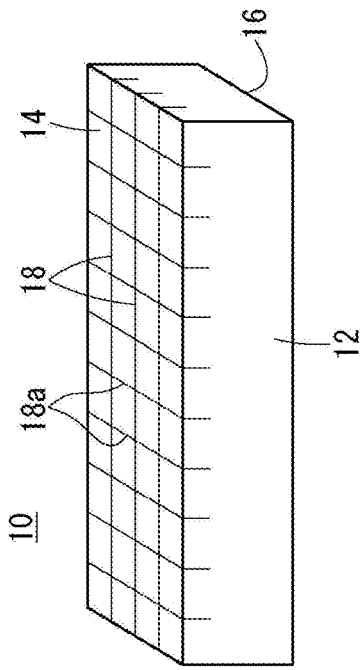
FIG. 3A is a perspective view illustrating an example of forming slits in the embolus material in FIG. 1A in a longitudinal direction thereof.
Figure 3B:
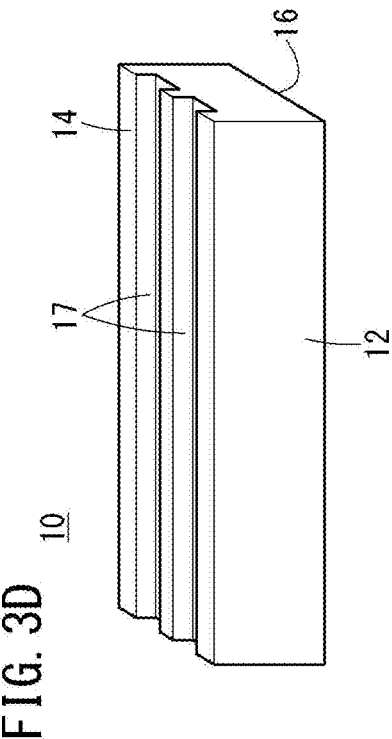
FIG. 3B is a perspective view illustrating an example of forming slits in a width direction.
Figure 3C:
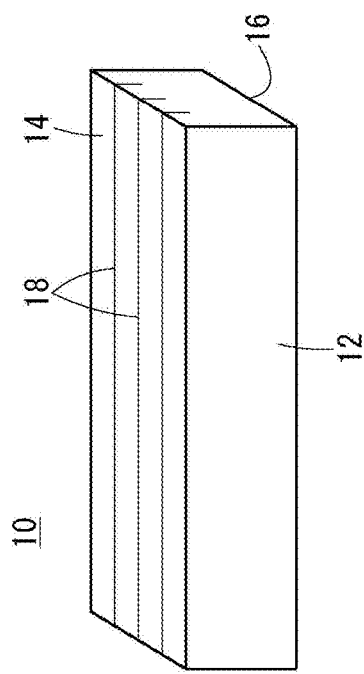
FIG. 3C is a perspective view illustrating an example of forming slits in a lattice shape.
Figure 3D:
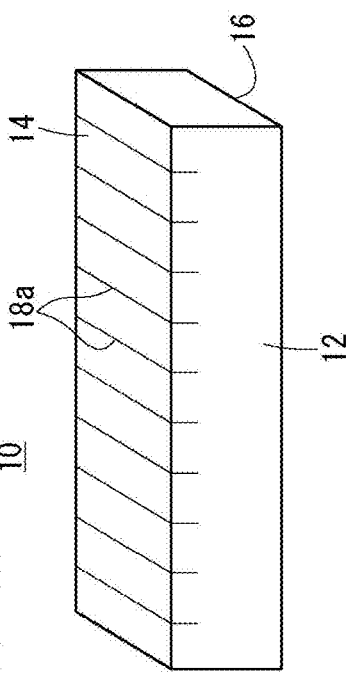
FIG. 3D is a perspective view illustrating an example of forming groove-shaped slits.

Next, as illustrated in FIG. 2B, slits 18 are formed on a surface of the thin plate-shaped hydrogel 12a. The slits 18 are formed by cutting a part of the surface side of the hydrogel 12a with a knife blade or laser light. Regarding a pattern of the slits 18, for example, as illustrated in FIG. 3A, the slits 18 may be slits that extend in a longitudinal direction of the filling body 12 may be formed. As illustrated in FIG. 3B, the slits 18a may alternatively be slits that extend in a direction intersecting the longitudinal direction of the filling body 12. Alternatively, lattice-shaped slits 18 and 18a as illustrated in FIG. 3C or groove-shaped slits 17 extending in the longitudinal direction of the filling body 12 as illustrated in FIG. 3D may be formed.

Next, as illustrated in FIG. 2C, the hydrogel 12a in which the slits 18 are formed is cleaned and dried, and is then cut into elongated thread-shaped pieces by a knife blade or a laser processing machine. Consequently, the embolus material 10 having the filling body 12 having an elongated and long shape is completed.

In addition to the method of manufacturing the embolus material 10 by forming the hydrogel in the above layered shape and then cutting the hydrogel, the embolus material 10 may be formed by polymerizing the hydrogel in a tube having a predetermined cross-sectional shape. Hereinafter, a description will be made of another method of manufacturing the embolus material 10 of the present embodiment.

Figure 4A:
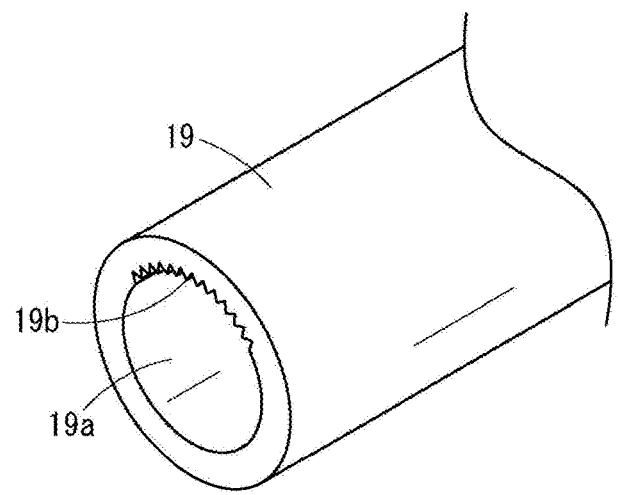
FIG. 4A is a cross-sectional perspective view illustrating a tube used for another method of manufacturing the embolus material of the first embodiment.

In this manufacturing method, a polymerization reaction of hydrogel is performed by using a tube 19 illustrated in FIG. 4A. The tube 19 has a plurality of projection portions 19b formed on a part of an inner circumferential portion 19a. The projection portions 19b extend in the axial direction of the tube 19, and are partially formed in a circumferential direction in a concentrated manner. That is, in this illustrated embodiment, the projection portions 19b do not extend around the entire 360° circumferential extent of the inner surface pf the tube 19. A portion facing the projection portions 19b is a smooth inner circumferential portion 19a. As the tube 19, for example, a tube produced from HYTREL (registered trademark) manufactured by DuPont may be used. The tube 19 can be dissolved in a predetermined solvent, and the filling body 12 can be easily taken out from the tube 19.

A raw material solution for hydrogel is filled into the tube 19. Next, a polymerization reaction (crosslinking reaction) of the raw material solution is performed in the tube 19 to form the hydrogel. Regarding the polymerization reaction, the raw material solution is polymerized according to a method of heating the tube 19 with a heating medium such as hot water (100° C.) for several hours, or a method of irradiating the tube 19 with ionizing radiation or ultraviolet rays.

Figure 4B:
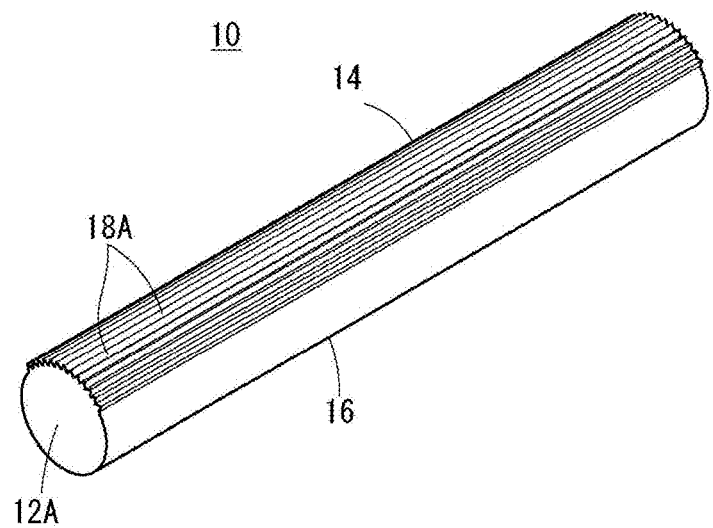
FIG. 4B is a perspective view illustrating an embolus material manufactured by using the tube in FIG. 4A.

Next, the tube 19 is dissolved in a predetermined solvent to be removed, and thus a filling body 12A illustrated in FIG. 4B is obtained. The filling body 12A has a plurality of grooves 18A in which the projection portions 19b of the tube 19 are reflected at one side portion (first side portion 14) of the tube 19 in the longitudinal direction. The first side portion 14 provided with the grooves 18A has a surface area larger than that of the other side portion (second side portion 16) formed of the smooth circumferential surface, and thus has a higher swelling rate. Next, the embolus material 10 of the present embodiment is obtained by cleaning and drying the filling body 12. The embolus material 10 manufactured as described above operates as follows.

Figure 5A:
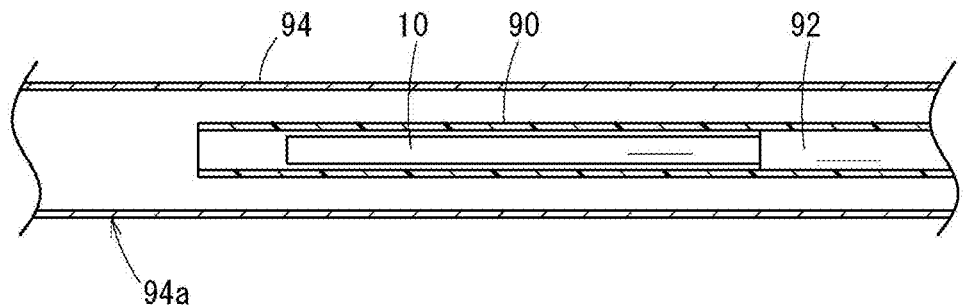
FIG. 5A is a schematic configuration diagram illustrating a step of moving a catheter to an embolus material indwelling position.
Figure 5B:
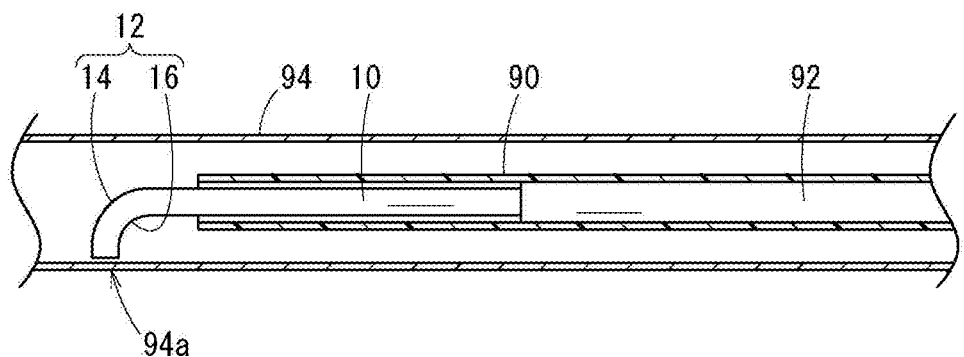
FIG. 5B is a schematic configuration diagram illustrating a step of pushing out the embolus material from the catheter.

As illustrated in FIG. 5A, the embolus material 10 in a dried state is inserted into or positioned in the catheter 90. As shown in FIG. 5A, the embolus material 10 (filling body 12) in the dried state in the catheter 90 exhibits a linear or straight overall configuration. The catheter 90 is inserted into, for example, the blood vessel 94 as a biological lumen. A distal end of the catheter 90 advances through the blood vessel 94 of a patient until reaching the indwelling position 94a in the blood vessel 94. When the catheter 90 reaches the indwelling position 94a, as illustrated in FIG. 5B, the embolus material 10 is pushed out by a pusher 92. The pushed-out embolus material 10 starts to be swollen due to contact with blood.

Figure 5C:
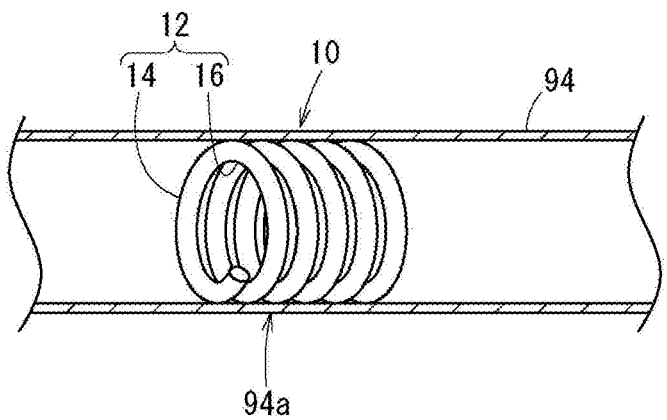
FIG. 5C is a schematic configuration diagram illustrating a state in which the embolus material inhibits a flow of a biological fluid.

In the filling body 12 of the embolus material 10, since a swelling rate of the first side portion 14 is higher than a swelling rate of the second side portion 16, the first side portion 14 side extends longer, the second side portion 16 becomes shorter, and this difference in length causes curving of the elongated filling body 12. As illustrated in FIG. 5C, the embolus material 10 pushed into the blood vessel 94 curves or deforms to form an annular or coil-shaped (spiral) three-dimensional structure. Since the three-dimensional structure is larger than an inner diameter of the blood vessel 94, the embolus material 10 is not pushed by a flow of the biological fluid and is clogged in the indwelling position 94a in the blood vessel 94. The embolus material 10 is not limited to the illustrated example, and a plurality of embolus materials are indwelled as necessary.

Next, the embolus material 10 indwelled at the indwelling position 94a and swollen fills the blood vessel 94 at the indwelling position 94a without a gap, and thus embolization is completed. The coil-shaped (spiral) curving of the embolus material 10 as illustrated is not essential to prevent movement in a biological lumen (blood vessel). The embolus material 10 is not necessarily required to be curved in a coil shape (spiral shape) and come into contact with an inner wall of the blood vessel 94 in a curved state, and can be configured to just come into contact with the inner wall of the blood vessel 94 while exhibiting stress due to deformation, thus exhibiting resistance to the flow of the biological fluid. In other words, even in a case where a diameter of the embolus material 10 is slightly smaller than the inner diameter of the blood vessel 94 and there is no space to be curved annularly, the embolus material 10 can embolize the inside of the blood vessel 94 without moving due to the flow of the biological fluid.

Figure 6:
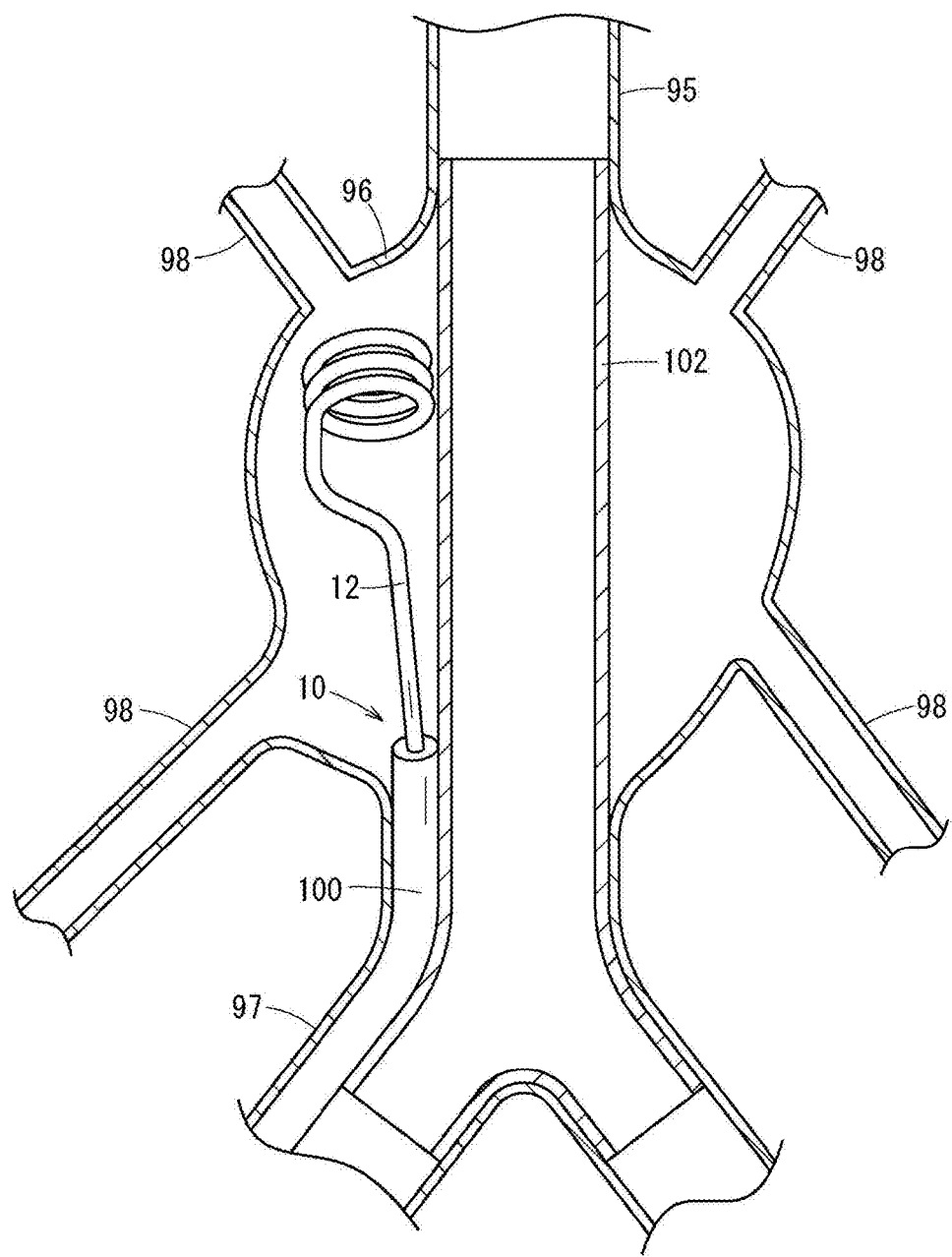
FIG. 6 is a schematic configuration diagram illustrating an example of using the embolus material in FIG. 1A for treating an aortic aneurysm.

As illustrated in FIG. 6, the embolus material 10 may be used not only for embolizing the blood vessel 94 but also for treating an aortic aneurysm 96. The aortic aneurysm 96 is treated according to stent graft treatment that is less invasive and less burdensome on patients. The stent graft treatment is treatment of inhibiting blood from flowing into the aortic aneurysm 96 by providing an artificial blood vessel (stent graft 102) in the aortic aneurysm 96.

However, it is known that the stent graft treatment causes several complications. One of the complications is Type 2 endoleak. Type 2 endoleak is a complication in which a blood flow that was flowing out in a forward direction from the aortic aneurysm 96 to a terminal blood vessel (bifurcated blood vessel 98) is reversed from the bifurcated blood vessel 98 side to the aortic aneurysm 96 due to the provision of the stent graft 102, and thus blood remains in the aortic aneurysm 96. If this is left unattended for a long period of time, the aortic aneurysm 96 may be enlarged by the reversed blood. Such Type 2 endoleak is said to occur in about 20% to 30% of patients who have undergone stent graft treatment in the long term.

Therefore, as illustrated, Type 2 endoleaks can be treated by indwelling the embolus material 10 of the present embodiment in the aortic aneurysm 96 and thus embolizing the aortic aneurysm 96. In this case, the catheter 100 is inserted into the aortic aneurysm 96 through the bifurcated blood vessel 98 connected to the aortic aneurysm 96 or from between the stent graft 102 and the iliac artery 97 (or the aorta 95), and the embolus material 10 is indwelled in the aortic aneurysm 96 via the catheter 100. The embolus material 10 is swollen in the aortic aneurysm 96 to embolize the aortic aneurysm 96, and thus inhibits blood from inflowing into the aortic aneurysm 96.

In the embolus material 10, the filling body 12 is curved due to the previously described swelling characteristic difference to form a coil-shaped structure, and is enlarged to be larger than the diameter of the bifurcated blood vessel 98 connected to the aortic aneurysm 96. Thus, the embolus material 10 does not enter the bifurcated blood vessel 98 unlike a liquid embolus material or a bead-like embolus material of the related art. Therefore, the embolus material 10 can safely embolize the aortic aneurysm 96 without causing a complication due to distal embolization via the bifurcated blood vessel 98. As mentioned above, the embolus material 10 of the present embodiment is suitable for treating Type 2 endoleaks.

As mentioned above, according to the embolus material 10 of the present embodiment, since the elongated filling body 12 is curved due to a difference in swelling characteristics of different parts of the elongated filling body 12, a curved portion is caught at a biological lumen, and thus it is possible to prevent movement of the embolus material due to a flow of a biological fluid. As a result, the embolus material to be swollen stays at a desired position and can thus inhibit a blood flow.

Second Embodiment

Figure 7A:
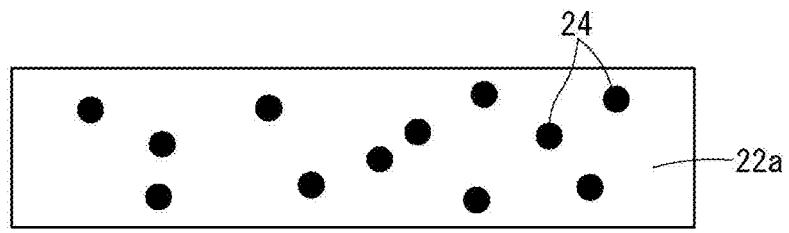
FIGS. 7A, 7B, and 7C are cross-sectional views illustrating a method of manufacturing an embolus material according to a second embodiment in a step order.
Figure 7B:
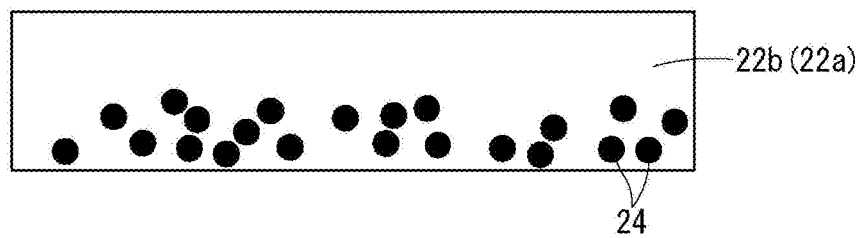
Figure 7C:
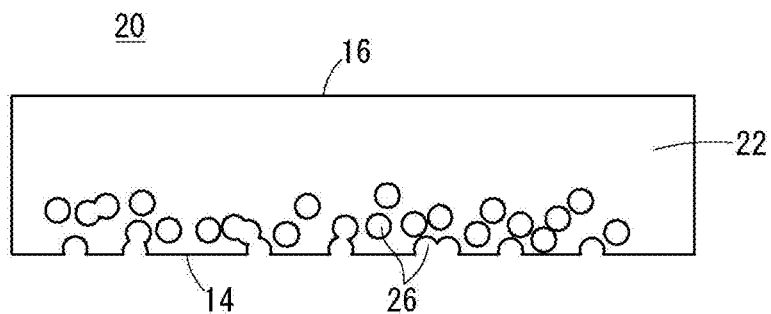

As illustrated in FIG. 7C, an embolus material 20 according to a second embodiment is formed of a porous filling body 22. Regarding a porous density (density of pores) of the filling body 22, the porous density of the first side portion 14 is higher than the porous density of the second side portion 16. Consequently, a surface area of the first side portion 14 is larger than a surface area of the second side portion 16, and thus a swelling rate of the first side portion 14 is also higher. The filling body 22 may be manufactured as follows.

First, as illustrated in FIG. 7A, a raw material solution 22a for the filling body 22 is prepared, and is poured into a mold. The raw material solution 22a of the present embodiment contains a pore forming agent 24 in addition to an ethylenically unsaturated monomer, a crosslinking agent, a polymerization initiator, and a solvent. As the ethylenically unsaturated monomer, the crosslinking agent, the polymerization initiator, and the solvent, the same materials as those in the first embodiment as described above may be used.

The pore forming agent 24 is made of a supersaturated soluble substance that cannot be completely dissolved in the raw material solution 22a, or a substance that is insoluble in the raw material solution 22a and soluble in a cleaning liquid. In a case where water-soluble particles are used for the pore forming agent 24, the raw material solution 22a may be appropriately mixed with an organic solvent to reduce the polarity of the solvent and thus to prevent the pore forming agent 24 from being dissolved. As the pore forming agent 24, specifically, for example, sodium chloride, potassium chloride, ice, sucrose, and sodium bicarbonate may be used. As the pore forming agent 24, it is preferable to use a substance that has a larger relative density than that of the raw material solution 22a and precipitates in the raw material solution 22a, or a substance that has a smaller relative density than that of the raw material solution 22a and floats in the raw material solution 22a. The pore forming agent 24 is dispersed as particles having a diameter of, for example, 500 µm or less in the raw material solution 22a.

The raw material solution 22a containing the pore forming agent 24 is stirred and uniformly suspended, and is then poured into a mold. In the present embodiment, a thin plate-shaped hydrogel may be formed, and a tube may be formed. As the tube, for example, a tube having a predetermined diameter produced from HYTREL (registered trademark) manufactured by DuPont may be used. Such a tube can be dissolved in a predetermined solvent, and the filling body 22 can be easily taken out from the tube.

Next, as illustrated in FIG. 7B, the raw material solution 22a is placed still for a predetermined time. Consequently, the particles of the pore forming agent 24 having a larger relative density than that of the raw material solution 22a precipitate, and the particles of the pore forming agent 24 gather near a bottom part of the mold. Next, the raw material solution 22a in which the pore forming agent 24 has precipitated is heated to start a polymerization reaction and to form hydrogel 22b. Consequently, a position of the pore forming agent 24 is fixed, and the hydrogel 22b containing a lot of the pore forming agent 24 at the bottom part is formed.

As a method of unevenly distributing the pore forming agent 24 in the raw material solution 22a, various methods other than the method of causing the pore forming agent 24 to precipitate may be employed. For example, the pore forming agent 24 may be unevenly distributed by an electric field by using particles having electric charge for the pore forming agent 24. In this case, for example, negatively charged particles composed of a polysaccharide such as an alginic acid and agarose may be used. For example, positively charged particles composed of gelatin may be used. By dispersing the particles as the pore forming agent 24 in the raw material solution 22a for the hydrogel and applying an electric field thereto, the pore forming agent 24 can be unevenly distributed in the raw material solution 22a. Next, a position of the pore forming agent 24 may be fixed by polymerizing the raw material solution 22a.

After the position of the pore forming agent 24 is fixed in the hydrogel 22b, the thread-like hydrogel 22b is taken out by dissolving and removing the tube. Next, as illustrated in FIG. 7C, the hydrogel 22b is cleaned with a cleaning liquid that can dissolve the pore forming agent 24. Consequently, the pore forming agent 24 is dissolved in the cleaning liquid and is thus removed from the hydrogel 22b. Since the pore forming agent 24 is dissolved and removed in the above-described way, pores 26 having shapes of the particles of the pore forming agent 24 are formed, and the porous hydrogel 22b is obtained. The pores 26 concentrate at a bottom part (first side portion 14) of the hydrogel 22b, and are slightly present near a top part (second side portion 16) of the hydrogel 22b. In other words, the size of the porous density is biased. By drying the thread-like hydrogel 22b, the filling body 22 having a high porous density on the first side portion 14 and a low porous density on the second side portion 16 is obtained. In a case of forming a thin plate-shaped hydrogel, the hydrogel in FIG. 7C may be cleaned and dried, and then cut into thin pieces to be formed into a thread-like shape.

As will be described later in detail, the embolus material 20 of the present embodiment may also be formed according to a method in which a hydrogel containing the pore forming agent 24 is stuck to a hydrogel not containing the pore forming agent 24 (refer to FIG. 12), or a method in which the hydrogel containing the pore forming agent 24 and the hydrogel not containing the pore forming agent 24 are polymerized to be stacked (refer to FIGS. 13A to 13C).

The embolus material 20 of the present embodiment includes the filling body 22 having a high porous density at the first side portion 14 and a low porous density at the second side portion 16. The first side portion 14 has a large surface area due to a large number of pores 26, and thus has a higher water infiltration rate than that of the second side portion 16. As a result, a swelling rate of the first side portion 14 is higher than a swelling rate of the second side portion 16, and can thus cause curving in the swelling process. Therefore, the embolus material 20 can also achieve the same effect as that achieved by the embolus material 10 of the first embodiment.

The embolus material 20 of the present embodiment is not limited the above description. For example, as illustrated in FIG. 7B, an embolus material may be used in which the pore forming agent 24 is not removed from the hydrogel 22b containing the pore forming agent 24. In this case, the pore forming agent 24 is cleaned while being careful not to leach the pore forming agent, and is then dried, and thus the embolus material is obtained. For cleaning of the hydrogel 22b, a supersaturated solution containing the components of the pore forming agent 24 may be used as a cleaning liquid. The hydrogel 22b may be cleaned with a cleaning liquid in which the pore forming agent 24 is less likely to be leached by mixing an organic solvent to reduce the polarity.

In the embolus material containing the pore forming agent 24, the pore forming agent 24 is dissolved and removed through contact with a biological fluid such as blood, and, thus, as illustrated in FIG. 7C, the embolus material 20 having a high porous density at the first side portion 14 is formed in a living body. The first side portion 14 is swollen relatively fast, and can thus cause curving. In this case, as the pore forming agent 24, for example, particles of sugar such as glucose or sucrose, or particles of an electrolyte salt such as salt may be used. It is preferable to use a low molecular weight substance as the pore forming agent 24 that is eluted into a living body. The low molecular weight substance can be diffused through the inside of the mesh structure of the hydrogel 22b forming the embolus material, and can thus be quickly leached. When an electrolyte is used as the pore forming agent 24, an ionic strength of the hydrogel 22b around the electrolyte is increased, and a swelling rate is further increased, which is preferable.

Third Embodiment

Figure 8A:
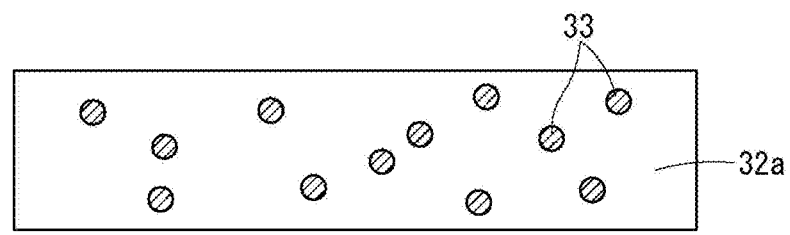
FIG. 8A is a cross-sectional view illustrating a method of manufacturing an embolus material according to a third embodiment.
Figure 8B:
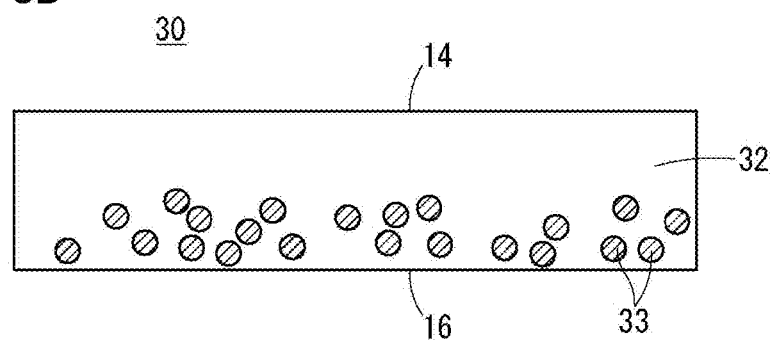
FIG. 8B is a cross-sectional view illustrating the embolus material according to the third embodiment.

As illustrated in FIG. 8B, an embolus material 30 according to the present embodiment has a structure in which insoluble particles 33 are unevenly distributed near the second side portion 16 of a filling body 32. In the embolus material 30, infiltration of water is hindered since the insoluble particles 33 are present at the second side portion 16. As a result, a swelling rate of the second side portion 16 is lower than a swelling rate of the first side portion 14, and thus the embolus material 30 is curved when coming into contact with water. In other words, the embolus material 30 of the present embodiment is curved by providing the structure of hindering infiltration of water at the second side portion 16.

A method of manufacturing the embolus material 30 will be described with reference to FIGS. 8A and 8B. First, as illustrated in FIG. 8A, the insoluble particles 33 are dispersed in a raw material solution 32a for a hydrogel. As the insoluble particles 33, for example, particles of barium sulfate, bismuth, tantalum, platinum, gold, silica, or polystyrene may be used.

Next, the raw material solution 32a in which the insoluble particles 33 are dispersed is injected into a mold such as a tube, and the tube is horizontally disposed and is placed still for a predetermined time. Consequently, as illustrated in FIG. 8B, the insoluble particles 33 float or precipitate due to the difference in relative density between the raw material solution 32a and the insoluble particles 33, and the insoluble particles 33 are unevenly distributed on a side portion (an upper side or a lower side) of the horizontally disposed mold.

The insoluble particles 33 may be unevenly distributed by applying an electric field. In this case, for example, the insoluble particles 33 may be particles having a surface potential. Specifically, for example, silica particles and polystyrene particles have a surface potential, and the insoluble particles 33 can be unevenly distributed by an electric field.

Next, the raw material solution 32a is heated to be polymerized, and thus forms the filling body 32 in which the insoluble particles 33 are unevenly distributed at the second side portion 16. Next, the mold (for example, a tube) is removed, and the filling body 32 is taken out, cleaned, and dried to obtain the embolus material 30 of the present embodiment.

Figure 12:
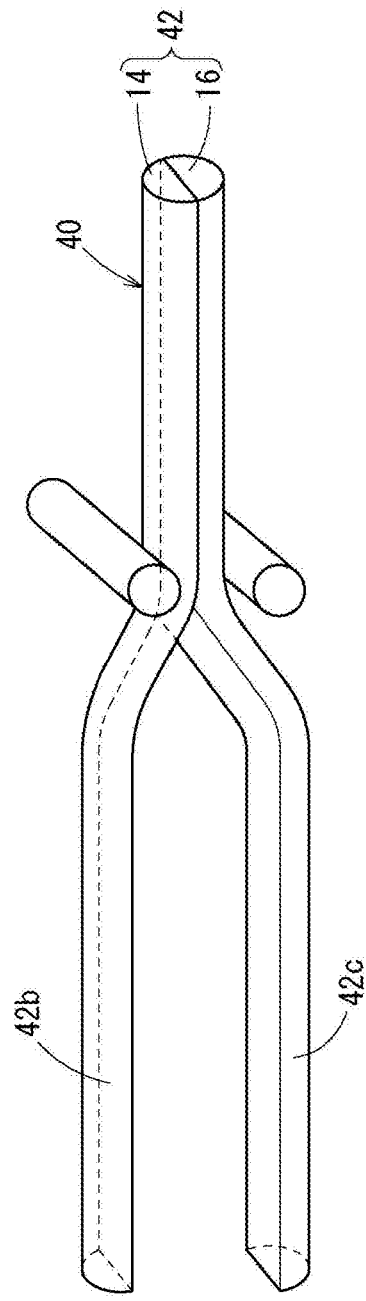
FIG. 12 is a schematic configuration diagram illustrating a method of manufacturing an embolus material according to Modification Example 2 of the fifth embodiment.
Figure 13A:
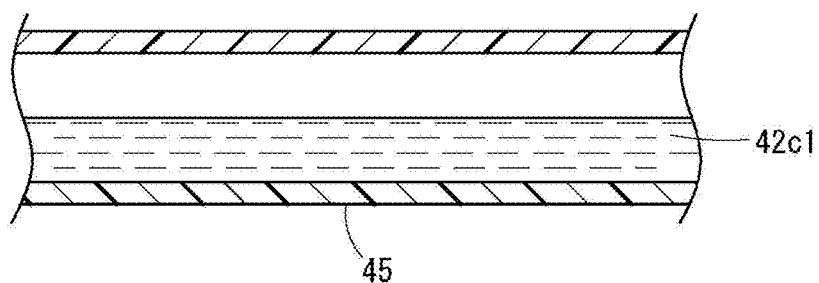
FIGS. 13A, 13B, and 13C are cross-sectional views illustrating a method of manufacturing an embolus material according to Modification Example 3 of the fifth embodiment in a step order.
Figure 13B:
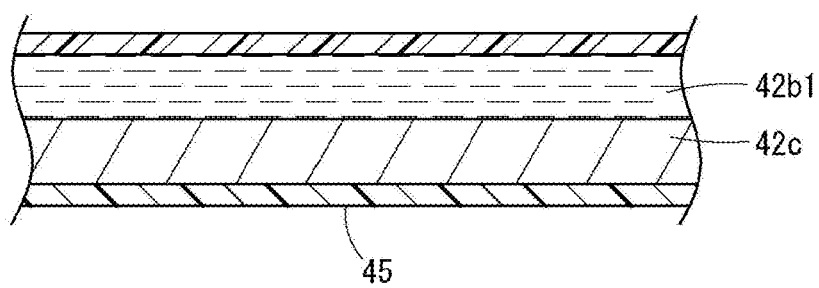
Figure 13C:
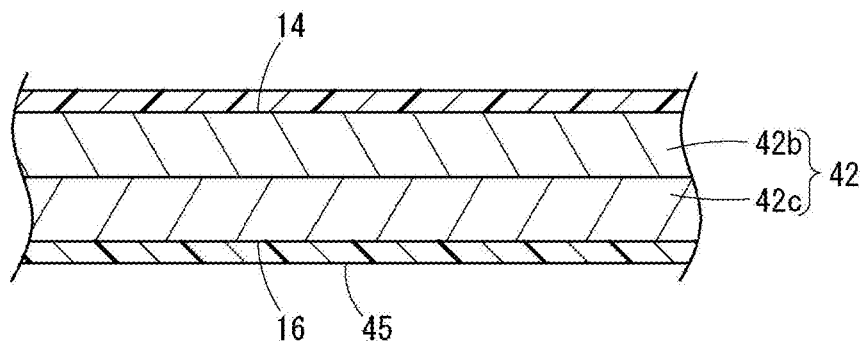

The embolus material 30 of the present embodiment may also be formed according to a method in which a hydrogel not containing the insoluble particles 33 is stuck to a hydrogel containing the insoluble particles 33 (refer to FIG. 12), or a method in which the hydrogel not containing the insoluble particles 33 and the hydrogel containing the insoluble particles 33 are polymerized to be stacked (refer to FIGS. 13A to 13C).

According to the embolus material 30 of the present embodiment, the insoluble particles 33 are unevenly distributed at the second side portion 16 of the filling body 32 made of a hydrogel. In the portion where the insoluble particles 33 are unevenly distributed, water is less likely to infiltrate, so that a swelling rate is low. In other words, a swelling rate of the second side portion 16 of the filling body 32 is relatively low compared with a swelling rate of the first side portion 14, and thus the embolus material 30 can be curved when being swollen. Consequently, the embolus material 30 can prevent outflow thereof due to a biological fluid in a biological lumen.

Instead of the insoluble particles 33, a thread-shaped structure extending in the longitudinal direction of the embolus material 30 may be added to a raw material solution for a hydrogel. As the thread-shaped structure, a structure having a lower expansion swelling ratio (equilibrium swelling degree) than that of a hydrogel may be used. The thread-shaped structure precipitates in a raw material solution to be unevenly distributed at the second side portion 16. The embolus material 30 including the thread-shaped structure can be curved since a swelling ratio of the second side portion 16 is lower than that of the first side portion 14.

Fourth Embodiment

Figure 9:
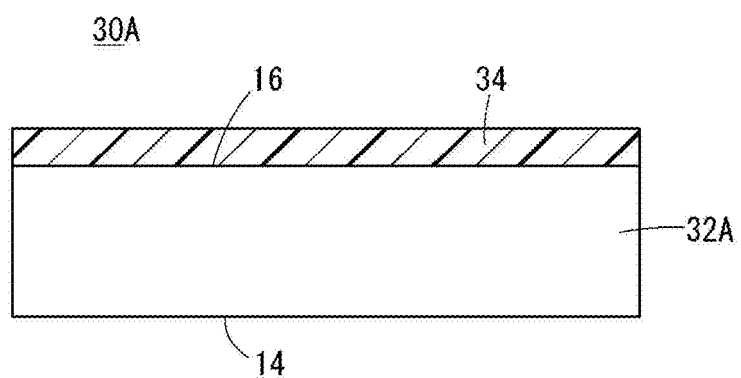
FIG. 9 is a cross-sectional view illustrating an embolus material according to a fourth embodiment.

As illustrated in a cross-sectional view of FIG. 9, an embolus material 30A according to the present embodiment includes a filling body 32A and a waterproof film 34. The filling body 32A may be made of a uniform hydrogel that includes a first side portion 14 that is a side extending in a longitudinal direction and a second side portion 16 extending parallel to the first side portion 14. Here, the second side portion 16 of the filling body 32A is covered with the waterproof film 34.

The waterproof film 34 may be made of a material inhibiting infiltration of water or a material of which a water infiltration rate is lower than that of the hydrogel forming the filling body 32. As such a material, for example, a film of cellulose or polylactic acid may be used.

The waterproof film 34 is formed by applying or adhering a material forming the waterproof film 34 to the hydrogel forming the filling body 32A. The hydrogel covered with the waterproof film 34 is cut into thread-like shapes, and thus the long filling body 32A that is elongated is obtained. The filling body 32A may be directly formed into a thread-like shape by polymerizing the hydrogel in a tube. In this case, the embolus material 30A of the present embodiment may be obtained by selectively applying the waterproof film 34 only to the second side portion 16 of the thread-like filling body 32A.

According to the embolus material 30A of the present embodiment configured as described above, the second side portion 16 is covered with the waterproof film 34, and thus the infiltration of water from the second side portion 16 into the filling body 32A is inhibited. A swelling rate of the first side portion 14 is higher than a swelling rate of the second side portion 16, and thus the filling body 32 can be curved in the swelling process. Therefore, the embolus material 30A can also achieve the same effect as that achieved by the embolus material 10 of the first embodiment.

Fifth Embodiment

Figure 10A:
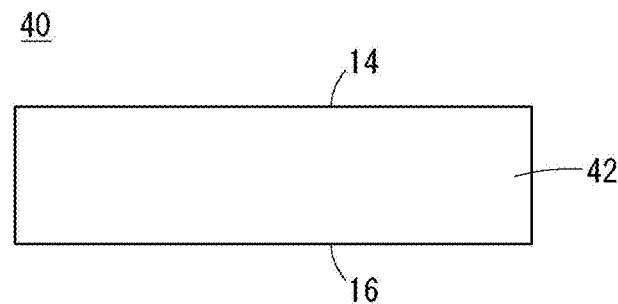
FIG. 10A is a cross-sectional view illustrating an embolus material according to a fifth embodiment.

As illustrated in FIG. 10A, an embolus material 40 according to the present embodiment includes a filling body 42 in which ionic strengths of a hydrogel are different from each other between the first side portion 14 and the second side portion 16. In the present embodiment, a polymer forming the hydrogel forming the filling body 42 contains a basic substituent such as a hydroxyl group or an amine group, or an acidic substituent such as a carboxyl group or a sulfate group. The polymer having such a basic substituent or an acidic substituent is also called a polyelectrolyte and is bonded to various cations or anions. A concentration (ionic strength) of an ion-active group bonded to the cations or the anions is high at the first side portion 14 in the filling body 42, and is inclined such that the ionic strength gradually decreases toward the second side portion 16.

A hydrogel containing a large amount of basic substituents or acidic substituents and having a higher ionic strength has a higher affinity for water, a faster water infiltration rate, and a faster swelling rate. Thus, in the filling body 42, the swelling rate of the first side portion 14 having a high ionic strength is higher than a swelling rate of the second side portion 16.

Figure 10B:
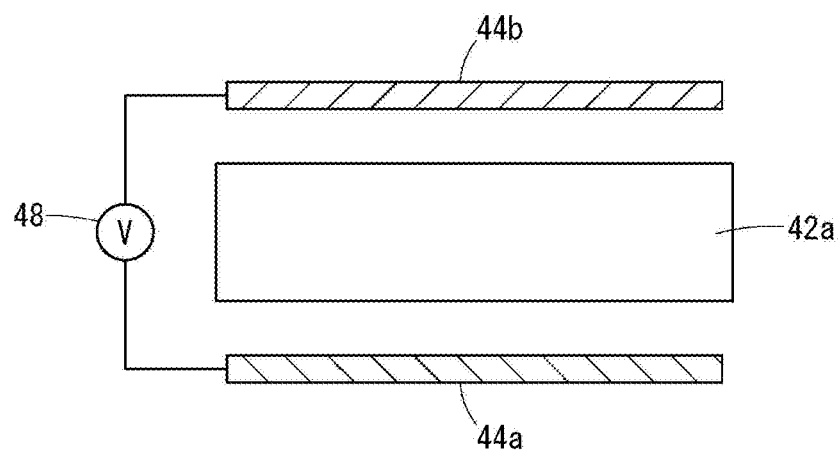
FIG. 10B is a schematic configuration diagram illustrating a method of manufacturing the embolus material according to the fifth embodiment.

For example, as illustrated in FIG. 10B, the filling body 42 is subjected to a polymerization reaction while applying an electric field to a raw material solution 42a for the hydrogel forming the filling body 42. Specifically, for example, a tube filled with the raw material solution 42a is disposed between a pair of electrodes 44a and 44b, and the polymerization reaction is performed while applying a voltage between the electrodes 44a and 44b and heating the tube with a heat medium such as boiling water. The raw material solution 42a contains only ion-active groups (substituents) bonded to either cations or anions. When a predetermined voltage is applied to the electrodes 44a and 44b from a power supply 48, an electric field is generated, and polymers containing the ion-active groups contained in the raw material solution 42a are attracted in a predetermined direction by the electric field. As a result, the polymers containing the ion-active groups gather at the first side portion 14, and a gradient of ionic strength is formed in the hydrogel obtained through the polymerization reaction.

Next, the hydrogel is taken out from the tube, and thus the thread-like or thread-shaped filling body 42 is obtained. The filling body 42 is cleaned and dried as appropriate, and thus the embolus material 40 of the present embodiment is obtained.

Also in the present embodiment, the hydrogel may be polymerized in a plate-shaped mold instead of using the tube. In this case, the plate-shaped hydrogel obtained through the polymerization reaction is cut into thin thread-like shapes to obtain the elongated and long shaped filling body 42.

Modification Example 1 of Fifth Embodiment

In Modification Example 1, the embolus material 40 (refer to FIG. 10A) has a gradient of ionic strength depending on the concentration of an electrolyte with which the filling body 42 is impregnated, instead of the hydrogel itself forming the filling body 42. Also in Modification Example 1, a concentration (ionic strength) of the electrolyte in the filling body 42 is high at the first side portion 14, and a concentration (ionic strength) of the electrolyte is low at the second side portion 16.

As the electrolyte with which the filling body 42 is impregnated, for example, a salt of ions of sodium, potassium, calcium, or magnesium, and a chlorine, an acetic acid, a citric acid, or a phosphoric acid may be used. A polyelectrolyte having an acidic substituent or a basic substituent may be used as the electrolyte.

In the embolus material 40 of the present modification example, there is a difference in osmotic pressure between the first side portion 14 having a high electrolyte concentration and the second side portion 16 having a low electrolyte concentration, and the first side portion 14 having a high electrolyte concentration attracts more water. As a result, a swelling rate of the first side portion 14 having a high electrolyte concentration is higher than a swelling rate of the second side portion 16, and thus the embolus material can be curved when being swollen.

In a method of manufacturing the embolus material 40 of the present embodiment, the embolus material may be manufactured by forming a hydrogel having a uniform ionic strength and contacting a solution containing a monomer or a polymer having an ion-active group with one side (first side portion 14) of the hydrogel.

Figure 11A:
FIG. 11A is a perspective view illustrating a tube used for manufacturing an embolus material according to Modification Example 1 of the fifth embodiment.

As illustrated in FIG. 11A, a raw material solution for the hydrogel is filled into a tube 45, and the tube 45 is heated for a predetermined time to polymerize the raw material solution and thus to form the filling body 42 made of the thread-like or thread-shaped hydrogel.

Figure 11B:
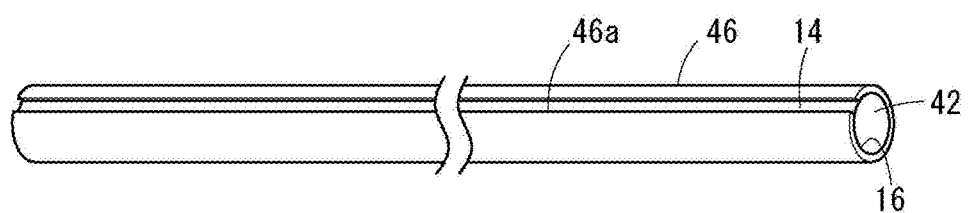
FIG. 11B is a perspective cross-sectional view illustrating a mask used for manufacturing the embolus material according to Modification Example 1 of the fifth embodiment.

Next, as illustrated in FIG. 11B, a mask 46 in which an opening portion 46a is formed in a portion corresponding to the first side portion 14 is formed on or provided on an outer peripheral surface of the filling body 42. Next, an electrolyte is infiltrated into the first side portion 14 of the filling body 42 by bringing a solution containing an electrolyte into contact with the first side portion 14 of the filling body 42 exposed to the opening portion 46a of the mask 46. Consequently, the filling body 42 having a gradient in ionic strength between the first side portion 14 and the second side portion 16 is obtained. In a case where the electrolyte is a polyelectrolyte, the infiltrated polyelectrolyte may be polymerized with the hydrogel forming the filling body 42 through reheating as necessary.

Modification Example 2 of Fifth Embodiment

In Modification Example 2, the embolus material 40 is manufactured by chemically or physically joining a plurality of hydrogels having different ionic strengths.

As illustrated in FIG. 12, a first hydrogel 42b having a relatively high ionic strength and a second hydrogel 42c having a relatively low ionic strength are separately produced. Here, each of the first hydrogel 42b and the second hydrogel 42c is formed as an elongated body having a semicircular section. The first and second hydrogels 42b and 42c may be produced by polymerizing a raw material solution having a predetermined composition to an appropriate hardness and then extruding the raw material solution.

Next, the first hydrogel 42b and the second hydrogel 42c are stuck to each other and are heated as appropriate, and the first hydrogel 42b and the second hydrogel 42c are joined through a polymerization reaction, to form the filling body 42. Next, the filling body 42 is cleaned and dried, and thus the embolus material 40 of the present embodiment is completed. In the present modification example, a portion made of the first hydrogel 42b having a high ionic strength serves as the first side portion 14, and a portion made of the second hydrogel 42c having a low ionic strength serves as the second side portion 16. In the above-described way, it is possible to obtain the embolus material 40 that is curved when being swollen.

In the present modification example, the first hydrogel 42b and the second hydrogel 42c may be formed in a thin plate shape and may be joined to each other to be then cut into thin thread-like or thread-shaped shapes such that the filling body 42 is formed.

Modification Example 3 of Fifth Embodiment

In Modification Example 3, the filling body 42 is formed by stacking hydrogels having different ionic strengths in layers by causing a polymerization reaction while sequentially pouring raw material solutions having different ionic strengths into a heated mold. In this case, the ionic strengths of the raw material solutions may be gradually increased or decreased to provide a gradient of ionic strength in the stacked hydrogel layers. The hydrogels formed in above-described way are cut into thread-like or thread-shaped shapes, and thus it is possible to obtain the filling body 42 having a gradient of ionic strength between the first side portion 14 and the second side portion 16.

Modification Example 3 may be applied to a manufacturing method using a tube. As illustrated in FIG. 13A, the tube 45 is prepared, and about a half amount of a raw material solution 42c1 is injected or introduced into the tube 45. Next, the second hydrogel 42c is formed by horizontally disposing the tube 45 in the entire length direction and polymerizing the raw material solution 42c1 in the tube 45.

Next, as illustrated in FIG. 13B, a raw material solution 42b1 is injected into a remaining space in the tube 45 in which the second hydrogel 42c is formed. The raw material solution 42b1 contains a larger amount of electrolyte than that of the second hydrogel 42c and thus has a higher ionic strength. Next, the raw material solution 42b1 is polymerized.

Consequently, as illustrated in FIG. 13C, it is possible to obtain the filling body 42 in which the first hydrogel 42b is stacked on, or side-by-side with respect to, the second hydrogel 42c. Next, the filling body 42 is taken out by dissolving and removing the tube 45 with a predetermined solvent, and the embolus material 40 of the present embodiment can be obtained by cleaning and drying the filling body 42.

Modification Example 4 of Fifth Embodiment

In Modification Example 4, a gradient of ionic strength may be provided according to a method in which the filling body 42 is made of a hydrogel having a polymer chain having an acidic ion-active group, and the second side portion 16 thereof is brought into contact with a low-ph solution to reduce an ionic strength near the second side portion 16. A gradient of ionic strength may be provided according to a method in which the filling body 42 is made of a hydrogel having a polymer chain having a basic ion-active group, and the second side portion 16 thereof is brought into contact with a high-ph solution to reduce an ionic strength near the second side portion 16.

Modification Example 4 may be performed by using a tube. In this case, the mask 46 illustrated in FIG. 11B may be used. In other words, the mask 46 in which the opening portion 46a is provided in the second side portion 16 is formed on the outer peripheral portion of the filling body 42. Thereafter, a low-ph or high-ph solution may be brought into contact with the second side portion 16 exposed to the opening portion 46a to reduce an ionic strength such that the embolus material 40 of the present embodiment is formed.

According to the embolus material 40 of the present embodiment manufactured in the methods including Modification Example 1 to Modification Example 4, an ionic strength of the filling body 42 differs depending on a location. In other words, in the filling body 42, a swelling rate of the first side portion 14 having a higher ionic strength is higher than a swelling rate of the second side portion 16. Consequently, curving can be caused in the swelling process of the embolus material 40. Therefore, the embolus material 40 can also achieve the same effect as that achieved by the embolus material 10 of the first embodiment.

Sixth Embodiment

Figure 14A:
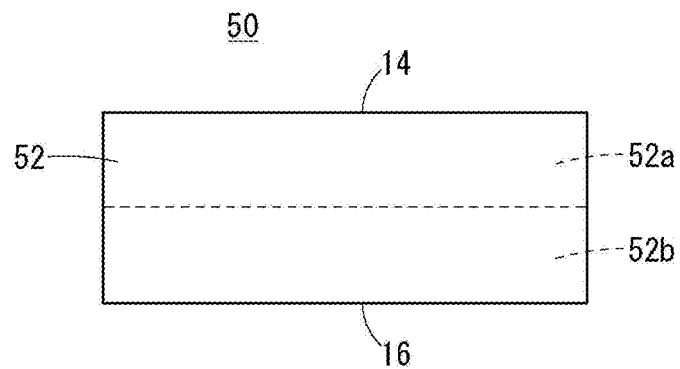
FIG. 14A is a cross-sectional view illustrating an embolus material according to a sixth embodiment.

As illustrated in FIG. 14A, an embolus material 50 according to the present embodiment is provided with a region 52a having high hydrophilicity (relatively high hydrophilicity) and a region 52b having low hydrophilicity (relatively low hydrophilicity) inside a filling body 52. The region 52a having high hydrophilicity contains a large number of molecules having a hydrophilic functional group in a polymer chain forming a hydrogel. The region 52b having low hydrophilicity contains a large number of hydrophobic molecules in a polymer chain forming the hydrogel. Examples of the hydrophilic functional group include a hydroxyl group, a sulfuric acid group, an amino group, and a carboxyl group. Examples of the hydrophobic functional group include a methyl group and a benzene group.

Figure 14B:
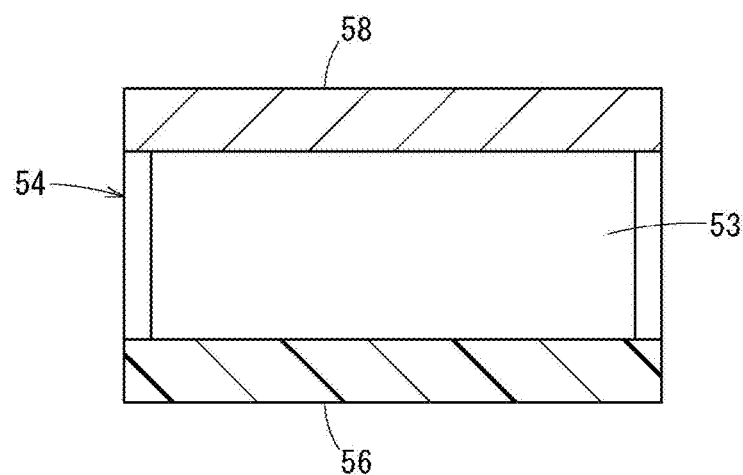
FIG. 14B is a schematic configuration diagram illustrating a method of manufacturing the embolus material according to the sixth embodiment.

As illustrated in FIG. 14B, the embolus material 50 is manufactured by performing a polymerization reaction in a container 54 interposed between a hydrophilic basal lamella 58 and a hydrophobic (or lipophilic) basal lamella 56 when a hydrogel forming the filling body 52 is polymerized. As the hydrophilic basal lamella 58, a basal lamella made of polyacrylamide, polyester, or the like may be used. As the hydrophobic basal lamella, for example, a basal lamella made of polyethylene or polystyrene may be used.

As a raw material solution 53, a solution is used which contains a hydrophilic polymer (for example, a polymer, a polysaccharide, or a polyol having electric charge) or a hydrophilic monomer (for example, acrylamide, a sugar, or a hydrophilic amino acid), and a hydrophobic polymer (for example, a hydrophobic polyamino acid or polyester) or a hydrophobic monomer (for example, a hydrophobic amino acid). In the raw material solution 53, when a polymerization reaction is performed in the container 54, the hydrophilic polymer or monomer gathers on the hydrophilic basal lamella 58 side, and the hydrophobic polymer or monomer gathers on the hydrophobic basal lamella 56 side.

Next, the raw material solution 53 is heated to be polymerized, and thus the hydrophilic region 52a and the hydrophobic region 52b are formed in the hydrogel. The hydrogel produced in the above-described way is dried and cut into pieces, and thus it is possible to obtain the filling body 52 in which the hydrophilic region 52a is formed at the first side portion 14 and the hydrophobic region 52b is formed at the second side portion 16.

The embolus material 50 of the present embodiment may also be formed according to a method in which a hydrophilic hydrogel is stuck to a hydrophobic hydrogel (refer to FIG. 12), or a method in which the hydrophilic hydrogel and the hydrophobic hydrogel are polymerized to be stacked (refer to FIGS. 13A to 13C).

In the embolus material 50 manufactured as described above, an infiltration rate of water is higher in the hydrophilic region 52a than in the hydrophobic region 52b. As a result, the first side portion 14 at which the hydrophilic region 52a is formed is swollen faster than the second side portion 16, and thus curving is caused in the swelling process. Therefore, the embolus material 50 can also achieve the same effect as that achieved by the embolus material 10 of the first embodiment. The first side portion 14 that contains a large number of hydrophilic molecules, also incorporates more water molecules in a polymer chain, and thus the equilibrium swelling degree also increases. Thus, in the embolus material 50, the first side portion 14 is also higher than the second side portion 16 in terms of equilibrium swelling degree. Therefore, the embolus material 50 can be maintained to be curved even in a case of being completely swollen.

Seventh Embodiment

Figure 15A:
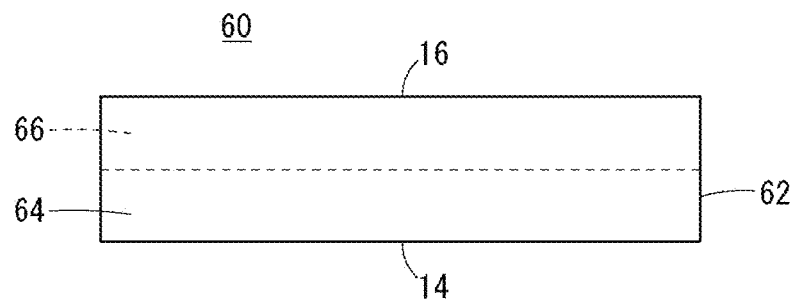
FIG. 15A is a cross-sectional view illustrating an embolus material according to a seventh embodiment.

As illustrated in FIG. 15A, an embolus material 60 according to the present embodiment includes a filling body 62 having a gradient of crosslinking density. The filling body 62 has a first region 64 having a low crosslinking density and a second region 66 having a high crosslinking density. In the filling body 62, the first side portion 14 is formed on the first region 64 side, and the second side portion 16 is formed on the second region 66 side.

In the second region 66 having a high crosslinking density, a mesh structure of polymer chains forming a hydrogel is fine, and thus it is difficult for water to be incorporated into the mesh structure such that swelling is difficult. In the first region 64, the mesh structure of the polymer chains is larger than in the second region 66, and swelling easily occurs. A swelling rate is higher in the first region 64 having a low crosslinking density and is lower in the second region 66 having a high crosslinking density. In other words, in the filling body 62, a swelling rate and an equilibrium swelling degree of the first side portion 14 are higher than a swelling rate and an equilibrium swelling degree of the second side portion 16.

Figure 15B:
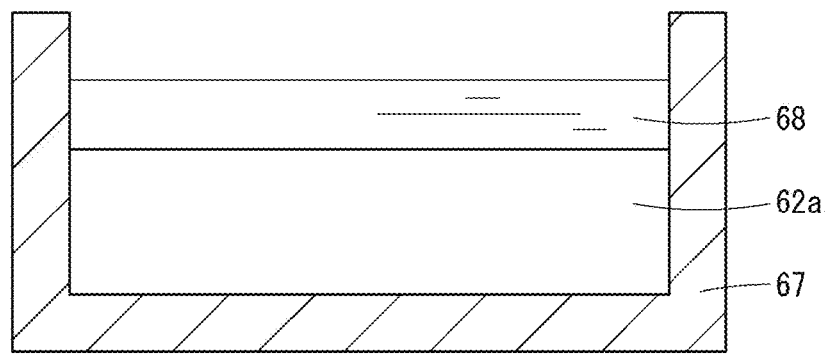
FIG. 15B is a schematic configuration diagram illustrating a method of manufacturing the embolus material according to the seventh embodiment.

The embolus material 60 is manufactured according to a method illustrated in FIG. 15B. In other words, a raw material solution is polymerized in a mold 67 to form a uniform hydrogel 62a. Next, as illustrated, a solution 68 containing a crosslinking agent is brought into contact with one surface (an upper surface in the figure) of the hydrogel 62a. Consequently, the crosslinking agent is infiltrated from the upper surface side of the hydrogel 62a. As a result, a concentration distribution occurs in the hydrogel 62a such that the concentration of the crosslinking agent becomes higher toward the upper surface. Next, the hydrogel 62a containing the crosslinking agent is heated, and thus the crosslinking agent is polymerized. Since a larger amount of polymers is crosslinked as a larger amount of the crosslinking agent is contained, a gradient of crosslinking density can be generated near the upper surface of the hydrogel 62a and near the bottom surface of the hydrogel 62a. Next, the hydrogel 62a is cut into thread-like or thread-shaped shapes and is dried, and thus the embolus material 60 is obtained.

A tube may be used to manufacture the embolus material 60 of the present embodiment. In this case, the tube 45 illustrated in FIG. 11A is used, and the uniform thread-like or thread-shaped hydrogel 62a is formed in the tube 45. Next, as illustrated in FIG. 11B, a side portion of the tube 45 is notched to form the mask 46 having the opening portion 46a. Next, a crosslinking agent is infiltrated into the hydrogel 62a exposed to the opening portion 46a, and then the hydrogel 62a is reheated to polymerize the crosslinking agent. Next, after the mask 46 is removed, the hydrogel 62a is cleaned and dried, and thus the embolus material 60 is obtained.

The embolus material 60 of the present embodiment may also be formed according to a method in which the hydrogels 62a having different crosslinking densities are stuck to each other (refer to FIG. 12), or a method in which raw material solutions containing different components are polymerized to be sequentially stacked (refer to FIGS. 13A to 13C).

According to the above-described embolus material 60 of the present embodiment, the filling body 62 is obtained such that a swelling rate of the first side portion 14 is higher than a swelling rate of the second side portion 16, and thus curving is caused in the swelling process. Consequently, it is possible to achieve the same effect as the effect achieved by the embolus material 10 of the first embodiment. Since an equilibrium swelling degree of the first side portion 14 is higher than an equilibrium swelling degree of the second side portion 16, the embolus material 60 can be maintained to be curved even after being swollen. Therefore, movement due to a flow of a biological fluid more hardly occurs, which is preferable.

Eighth Embodiment

Figure 16:
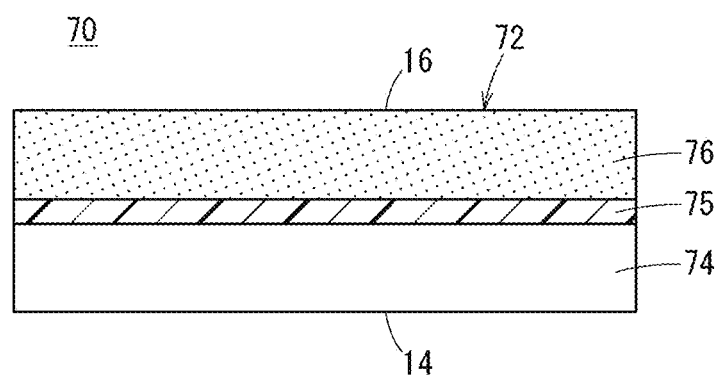
FIG. 16 is a cross-sectional view illustrating an embolus material according to an eighth embodiment.

As illustrated in FIG. 16, an embolus material 70 according to the present embodiment includes a filling body 72 in which a polymer concentration differs. A low concentration region 74 and a high concentration region 76 are formed in the filling body 72. The first side portion 14 is formed on the low concentration region 74 side, and the second side portion 16 is formed on the high concentration region 76 side. The concentration of a polymer forming a skeleton of a hydrogel is relatively low in the low concentration region 74, and the concentration of the polymer forming the skeleton of the hydrogel is relatively high in the high concentration region 76.

In the region having a high polymer concentration, an infiltration rate of water is low, and thus a swelling rate is low. On the other hand, in the region having a low polymer concentration, an infiltration rate of water is high, and thus a swelling rate is high. Therefore, a swelling rate of the first side portion 14 near the low concentration region 74 of the filling body 72 is higher than a swelling rate of the second side portion 16 near the high concentration region 76.

The low concentration region 74 (first hydrogel layer) and the high concentration region 76 (second hydrogel layer) may be formed differently by adjusting a ratio between a solvent and a monomer in a raw material solution for a hydrogel forming the filling body 72. That is, the hydrogel layer forming the high concentration region 76 is formed by polymerizing the raw material solution containing a small amount of the solvent and a high concentration of the monomer. The hydrogel layer forming the low concentration region 74 is formed by pouring a raw material solution containing a low concentration of the monomer and polymerizing the raw material solution. Thereafter, the first hydrogel layer and the second hydrogel layer may be adhered to each other via an adhesive layer 75, and a hydrogel in which the high concentration region 76 and the low concentration region 74 are stacked is obtained.

Next, the hydrogel in which the high concentration region 76 and the low concentration region 74 are stacked is cut into thread-like or thread-shaped shapes and is dried, and thus manufacturing of the embolus material 70 of the present embodiment is completed.

The embolus material 70 of the present embodiment may also be formed according to a method in which a hydrogel having a low polymer concentration is stuck to a hydrogel having a high polymer concentration (refer to FIG. 12), or a method in which the hydrogel having a low polymer concentration and the hydrogel having a high polymer concentration are polymerized to be stacked (refer to FIGS. 13A to 13C).

According to the above-described embolus material 70 of the present embodiment, a swelling rate of the first side portion 14 of the filling body 72 is higher than a swelling rate of the second side portion 16, and thus curving can be caused in the swelling process. Consequently, the embolus material 70 can also achieve the same effect as the effect achieved by the embolus material 10 of the first embodiment. In the embolus material 70, a larger amount of water can be incorporated into the region having a high polymer density, and thus an equilibrium swelling degree increases. Therefore, when the embolus material 70 is brought into contact with water, the first side portion 14 first extends more quickly than the second side portion 16 and causes curving, but, in the end, a swelling ratio of the second side portion 16 is higher than that of the first side portion 14. As a result, in a state in which the embolus material 70 is swollen, the second side portion 16 extends longer such that the embolus material 70 is maintained in a curved state.

The embolus material and the method of manufacturing the same according to the present invention are not limited to the embodiments, and may employ various configurations without departing from the spirit of the present invention.

The above description is summarized in the following appendices.

APPENDIX 1

An embolus material that is indwelled in a biological lumen to inhibit a flow of a biological fluid, the embolus material including:
a long filling body that is made of a material which is swollen when the material is brought into contact with the biological fluid,
in which the filling body has a first side portion and a second side portion in a radial direction of the filling body, and the first side portion and the second side portion have a difference in swelling characteristics.

APPENDIX 2

The embolus material according to Appendix 1, in which the difference in swelling characteristics is a difference in swelling rate.

APPENDIX 3

The embolus material according to Appendix 1, in which the difference in swelling characteristics is a difference in equilibrium swelling degree.

APPENDIX 4

The embolus material according to Appendix 2, in which a surface area of the first side portion is larger than a surface area of the second side portion.

APPENDIX 5

The embolus material according to Appendix 2, in which the first side portion is provided with a slit.

APPENDIX 6

The embolus material according to Appendix 2, in which a porous density of the first side portion is higher than a porous density of the second side portion.

APPENDIX 7

The embolus material according to Appendix 2, in which a pore forming agent that is leached to form a porous structure by coming into contact with the biological fluid is contained on a first side portion side of the filling body.

APPENDIX 8

The embolus material according to Appendix 2, in which insoluble particles that are not dissolved in the biological fluid are contained on a second side portion side of the filling body.

APPENDIX 9

The embolus material according to Appendix 2 or 3, in which a thread-like structure made of a material having an equilibrium swelling degree lower than an equilibrium swelling degree of the filling body is included on the second side portion side of the filling body.

APPENDIX 10

The embolus material according to Appendix 2, in which the second side portion is covered with a waterproof film.

APPENDIX 11

The embolus material according to Appendix 2, in which an ionic strength of the first side portion is higher than an ionic strength of the second side portion.

APPENDIX 12

The embolus material according to Appendix 2 or 3, in which the first side portion contains a larger amount of hydrophilic polymers than the second side portion.

APPENDIX 13

The embolus material according to Appendix 2 or 3, in which a polymer concentration of the second side portion is higher than a polymer concentration of the first side portion.

APPENDIX 14

The embolus material according to Appendix 3, in which a crosslinking density of the second side portion is higher than a crosslinking density of the first side portion.

APPENDIX 15

The embolus material according to any one of Appendixes 1 to 14, in which the filling body is indwelled in a aneurysm part of a blood vessel via a catheter.

APPENDIX 16

A method of manufacturing an embolus material that is indwelled in a biological lumen to inhibit a flow of a biological fluid, the method including:
a step of preparing a raw material solution for a hydrogel;
a step of forming the hydrogel by polymerizing the raw material solution; and
a step of increasing or decreasing a swelling rate of a part of the hydrogel.

APPENDIX 17

The method of manufacturing an embolus material according to Appendix 16, in which, in the step of increasing the swelling rate, processing for increasing a surface area of the part of the hydrogel is performed.

APPENDIX 18

The method of manufacturing an embolus material according to Appendix 16, in which, in the step of increasing the swelling rate, a gradient of ionic strength is caused by bringing a solution containing an electrolyte into contact with a part of the hydrogel.

APPENDIX 19

The method of manufacturing an embolus material according to Appendix 16, in which, in the step of decreasing the swelling rate, a difference in infiltration rate of water is provided by covering a part of the hydrogel with a waterproof film.

APPENDIX 20

The method of manufacturing an embolus material according to Appendix 16, in which, in the step of decreasing the swelling rate, a gradient of crosslinking density is caused by performing a polymerization reaction after a crosslinking agent is infiltrated into a part of the hydrogel.

APPENDIX 21

A method of manufacturing an embolus material that is indwelled in a biological lumen to inhibit a flow of a biological fluid, the method including:
a step of preparing a raw material solution for a hydrogel containing a plurality of compositions;
a step of unevenly distributing some of the compositions in a part of the raw material solution; and
a step of fixing uneven distribution of some of the compositions by polymerizing the raw material solution to form a hydrogel.

APPENDIX 22

The method of manufacturing an embolus material according to Appendix 21, in which the raw material solution contains water-soluble particles or water-insoluble particles as an additive, and the additive is unevenly distributed by precipitating the additive.

APPENDIX 23

The method of manufacturing an embolus material according to Appendix 21, in which the raw material solution contains particles having a surface potential as an additive, and the additive is unevenly distributed by applying an electric field to the raw material solution.

APPENDIX 24

The method of manufacturing an embolus material according to Appendix 22, in which a porous portion is formed in a part of the hydrogel by eluting the additive after the hydrogel is formed.

APPENDIX 25

The method of manufacturing an embolus material according to Appendix 21, in which the raw material solution contains a polyelectrolyte, and the polyelectrolyte is unevenly distributed by applying an electric field to the raw material solution.

APPENDIX 26

The method of manufacturing an embolus material according to Appendix 21, in which the raw material solution contains a hydrophilic polymer or monomer and a hydrophobic polymer or monomer, and the hydrophilic polymer or monomer and the hydrophobic polymer or monomer are unevenly distributed by bringing the raw material solution into contact with a hydrophilic basal lamella and a hydrophobic basal lamella.

APPENDIX 27

A method of manufacturing an embolus material that is indwelled in a biological lumen to inhibit a flow of a biological fluid, the method including:
a step of preparing a raw material solution for a hydrogel;
a step of causing a gradient of ionic strength or concentration of a hydrophilic polymer or a hydrophilic monomer in the raw material solution; and
a step of forming a hydrogel by polymerizing the raw material solution in which the gradient of concentration is caused.

APPENDIX 28

The method of manufacturing an embolus material according to Appendix 27, in which, in the step of causing the gradient of ionic strength of the raw material solution, an electric field is applied to the raw material solution.

APPENDIX 29

The method of manufacturing an embolus material according to Appendix 27, in which, in the step of causing the gradient of concentration of the hydrophilic polymer or the hydrophilic monomer in the raw material solution, the raw material solution is brought into contact with a hydrophobic basal lamella and a hydrophilic basal lamella disposed to face each other.

APPENDIX 30

A method of manufacturing an embolus material that is indwelled in a biological lumen to inhibit a flow of a biological fluid, the method including:
a step of forming a first hydrogel layer; and
a step of forming a second hydrogel layer having swelling characteristics that are different from swelling characteristics of the first hydrogel layer on the first hydrogel layer.

APPENDIX 31

A method of manufacturing an embolus material that is indwelled in a biological lumen to inhibit a flow of a biological fluid, the method including:
a step of forming a first hydrogel;
a step of forming a second hydrogel having swelling characteristics that are different from swelling characteristics of the first hydrogel; and
a step of joining the second hydrogel to the first hydrogel.

APPENDIX 32

An embolus method of indwelling an embolus material in a biological lumen to inhibit a flow of a biological fluid, the embolus material including a long filling body made of a material that is swollen when being brought into contact with the biological fluid, the filling body having a first side portion and a second side portion in a radial direction of the filling body, and the first side portion and the second side portion having different swelling characteristics.

APPENDIX 33

The embolus method according to Appendix 32, in which the embolus material is indwelled in the biological lumen by using a catheter.

What is claimed is:

1. An embolus material configured to be indwelled in a biological lumen to inhibit flow of a biological fluid in the biological lumen, the embolus material comprising:
an elongated filling body that is made of a material that swells when brought into contact with the biological fluid, the elongated filling body possessing opposite ends spaced apart from one another in a longitudinal direction of the elongated filling body;
the elongated filling body including a first side portion and a second side portion that both extend along the longitudinal direction of the elongated filling body so that each of plural planes spaced apart from one another along the longitudinal direction, perpendicular to the longitudinal direction and passing through the first side portion also pass through the second side portion; and
the first side portion and the second side portion each having swelling characteristics, the swelling characteristics of the first side portion of the elongated filling body at each of the planes being different from the swelling characteristics of the second side portion of the elongated filling body.

2. The embolus material according to claim 1, wherein the difference in the swelling characteristics between the first side portion of the elongated filling body and the second side portion of the elongated filling body is a difference in swelling rate.

3. The embolus material according to claim 2, wherein the first side portion of the elongated filling body and the second side portion of the elongated filling body each include a surface area, the surface area of the first side portion being greater than the surface area of the second side portion.

4. The embolus material according to claim 2, wherein the first side portion of the elongated filling body and the second side portion of the elongated filling body each include a porous density, the porous density of the first side portion greater than the porous density of the second side portion.

5. The embolus material according to claim 2, wherein the first side portion of the elongated filling body includes a pore forming agent that is leached to form a porous structure by coming into contact with the biological fluid.

6. The embolus material according to claim 2, wherein the second side portion of the elongated filling body incudes insoluble particles that are not dissolved in the biological fluid.

7. The embolus material according to claim 2, wherein a thread-shaped structure made of a material having an equilibrium swelling degree less than an equilibrium swelling degree of the elongated filling body is included on a side of the elongated filling body at which is located the second side portion of the elongated filling body.

8. The embolus material according to claim 2, wherein the second side portion of the elongated filling body is covered with a waterproof film.

9. The embolus material according to claim 2, wherein an ionic strength of the first side portion of the elongated filling body is higher than an ionic strength of the second side portion of the elongated filling body.

10. The embolus material according to claim 1, wherein the difference in the swelling characteristics between the first side portion of the elongated filling body and the second side portion of the elongated filling body is a difference in equilibrium swelling degree.

11. An embolus material configured to be indwelled in a biological lumen to inhibit flow of a biological fluid in the biological lumen, the embolus material comprising:

an elongated filling body that is made of a material that swells when brought into contact with the biological fluid, the elongated filling body possessing oppositely located first and second ends that are spaced apart from one another along a longitudinal direction of the elongated filling body, the elongated filling body including a central axis extending along the longitudinal direction of the elongated filling body;

the elongated filling body including a first side portion and a second side portion that both extend along the longitudinal direction of the elongated filling body, the first side portion including a first end and a second end, the second side portion including a first end and a second end;

the first side portion and the second side portions being located along the longitudinal direction of the elongated filling body such that a first plane perpendicular to the central axis passes through the first end of the first side portion and the first end of the second side portion, and a second plane perpendicular to the central axis passes through the second end of the first side portion and the second end of the second side portion; and the first side portion and the second side portion each having swelling characteristics, the swelling characteristics of the entirety of the first side portion of the elongated filling body being different from the swelling characteristics of the entirety of the second side portion of the elongated filling body.

12. The embolus material according to claim 11, wherein the difference in the swelling characteristics between the first side portion of the elongated filling body and the second side portion of the elongated filling body is a difference in swelling rate.

13. The embolus material according to claim 11, wherein the difference in the swelling characteristics between the first side portion of the elongated filling body and the second side portion of the elongated filling body is a difference in equilibrium swelling degree.

14. The embolus material according to claim 11, wherein the first side portion of the elongated filling body and the second side portion of the elongated filling body each include a surface area, the surface area of the first side portion being greater than the surface area of the second side portion.

15. The embolus material according to claim 11, wherein the first side portion extends from the first end of the elongated filling body to the second end of the elongated filling body.

16. An embolus material configured to be indwelled in a biological lumen to inhibit flow of a biological fluid in the biological lumen, the embolus material comprising:

an elongated filling body that is made of a material that swells when brought into contact with the biological fluid, the elongated filling body possessing oppositely located first and second ends that are spaced apart from one another along a longitudinal direction of the elongated filling body;

the elongated filling body including a first side portion and a second side portion that extend along opposite sides of the elongated filling body in the longitudinal direction of the elongated filling body, the first side portion extending in the longitudinal direction from the first end of the elongated filling body toward the second end of the elongated filling body, the second side portion extending in the longitudinal direction from the first end of the elongated filling body toward the second end of the elongated filling body; and the first side portion and the second side portion each having swelling characteristics, the swelling characteristics of the entirety of the first side portion of the elongated filling body being different from the swelling characteristics of the entirety of the second side portion of the elongated filling body.

17. The embolus material according to claim 16, wherein the difference in the swelling characteristics between the first side portion of the elongated filling body and the second side portion of the elongated filling body is a difference in swelling rate.

18. The embolus material according to claim 16, wherein the difference in the swelling characteristics between the first side portion of the elongated filling body and the second side portion of the elongated filling body is a difference in equilibrium swelling degree.

19. The embolus material according to claim 16, wherein the first side portion of the elongated filling body and the second side portion of the elongated filling body each include a surface area, the surface area of the first side portion being greater than the surface area of the second side portion.

20. The embolus material according to claim 16, wherein the first side portion extends from the first end of the elongated filling body to the second end of the elongated filling body.

* * * * *